United States Patent [19]

Takahara et al.

[11] Patent Number: 6,013,526
[45] Date of Patent: *Jan. 11, 2000

[54] MODIFIED PROTEIN FOR GENE TRANSFER AND PROCESS FOR PRODUCING THE SAME

[75] Inventors: Yoshiyuki Takahara; Naoyuki Yamada; Masao Motoki, all of Kawasaki, Japan

[73] Assignees: Ajinomoto Co., Inc.; Drug Delivery System Institute, Ltd., both of Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/927,087

[22] Filed: Sep. 10, 1997

Related U.S. Application Data

[63] Continuation of application No. 08/536,280, Sep. 29, 1995, abandoned.

[30] Foreign Application Priority Data

Sep. 29, 1994 [JP] Japan ................................. 6-270102

[51] Int. Cl.$^7$ ............................ C12N 15/00; A61K 48/00
[52] U.S. Cl. ........................ 435/455; 435/193; 435/69.1; 435/320.1; 435/325; 536/23.1; 514/44; 424/93.21; 530/395
[58] Field of Search .................................. 435/193, 69.1, 435/325, 320.1, 455, 465; 536/23.21; 524/59.1, 59.2; 935/32, 57, 71; 530/395; 424/93.21

[56] References Cited

U.S. PATENT DOCUMENTS

| | | | |
|---|---|---|---|
| 5,326,559 | 7/1994 | Milla | 424/85.2 |
| 5,420,025 | 5/1995 | Takagi et al. | 435/193 |
| 5,630,996 | 5/1997 | Reno et al. | 424/1.49 |
| 5,736,387 | 4/1998 | Paul et al. | 435/320.1 |

FOREIGN PATENT DOCUMENTS

| | | |
|---|---|---|
| WO 91/17773 | 11/1991 | WIPO . |
| WO 92/05250 | 4/1992 | WIPO . |
| WO 92/13570 | 8/1992 | WIPO . |
| WO 92/17210 | 10/1992 | WIPO . |
| WO 96/10089 | 4/1996 | WIPO . |

OTHER PUBLICATIONS

Database WPI, Derwent Publications, AN 95–196323, JP 07–111897, May 2, 1995.
Adv. Protein Chem., vol. 31, pp. 1–133, 1977, J. E . Folk, et al., "The ε–(gamma–Glutamyl)Lysine Crosslink and the Catalytic Role of Transglutaminases".
Adv. Enzymol., vol. 38, 1973, pp. 109–191, J. E. Folk, et al., "Molecular and Catalytic Properties of Transglutaminases".
Handbook of Biochemistry and Molecular Biology, vol. 2, pp. 669–685, Laszlo Lorand, et al., "Endo–gamma–Glutamine:ε–Lysine Transferases Enzymes Which Cross–Link Proteins".
Biochemistry, vol. 16, No. 25, 1977, pp. 5495–5501, Takashi Abe, et al., "Rabbit Liver Transglutaminase: Physical, Chemical, and Catalytic Properties".
Biochimica et Biophysica Acta, vol. 522, 1978, pp. 74–83, Stephen C. Brenner, et al., "Human Erythrocyte Transglutaminase Purification and Properties".
Agric. Biol. Chem., vol. 53, No. 10, pp. 2613–2617, 1989, Hiroyasu Ando, et al., "Purification and Characteristics of a Novel Transglutaminase Derived from Microorganisms".
Biosci. Biotech. Biochem., vol. 58, No. 1, pp. 82–87, 1994, Kinya Washizu, et al., "Molecular Cloning of the Gene for Microbial Transglutaminase from Streptoverticillium and Its Expression in Streptomyces Lividans".
Biochemistry, vol. 23, 1984, pp. 3759–3765, Sau–chi Betty Yan, et al., "Neoglycoproteins: In Vitro Introduction of Glycosyl Units at Glutamines in β–Casein Using Transglutaminase".
Biochem. J., vol. 273, 1991, pp. 73–78, Peter J. Coussons, et al., "Selective Modification by Transglutaminase of a Glutamine Side Chain in the Hinge Region of the Histidine–388–Glutamine Mutant of Yeast Phosphoglycerate Kinase".
The Journal of Biological Chemistry, vol. 262, No. 10, Apr. 5, 1987, pp. 4429–4432, George Y. Wu, et al., "Receptor–Mediated in Vitro Gene Transformation by a Soluble DNA Carrier System".
The Journal of Biological Chemistry, vol. 263, No. 29, Oct. 15, 1988, pp. 14621–14624, George Y. Wu, et al., "Receptor–Mediated Gene Delivery and Expression in Vivo".
Bio/Technology, vol. 8, Apr. 1990, 343–346, Robert J. Goodson, et al., "Site–Directed Pegylation of Recombinant Interleukin–2 at Its Glycosylation Site".
Proc. Natl. Acad. Sci. USA, vol. 84, pp. 1487–1491, Mar. 1987, Nandini V. Katre, et al., "Chemical Modification of Recombinant Interleukin 2 by Polyethylene Glycol Increases Its Potency in the Murine Meth a Sarcoma Model".
The Journal of Immunology, vol. 141, No. 12, pp. 4224–4228, Dec. 15, 1988, Masato Ogata, et al., "Il–2–Pe40 is Cytotoxic for Activated T Lymphocytes Expressing IL–2 Receptors".
Molecular & Cellular Biochemistry, vol. 20, No. 2, Jun. 28, 1978, pp. 67–75, Hans Bohn, "The Human Fibrin–Stabilizing Factors".
Anderson, et al. Human Gene Therapy 1:327–62, 1990.
Venkatesh et al. PNAS 87:8746–8750, 1990.
Meyer et al., Gene 129:263–268, 1993.
Henderson's Dictionary, 10$^{th}$ Edition 1990. E. Lawrence, Ed. Wiley & Sons. p. 207 Col 2 Lines 43–50.
Wagner et al. PNAS 89:6099–6103, 1992.
Waters et al., Eur. J. Immunol. 20:785–791, 1990.
Zatloukal et al. Ann. N.Y. Acad. Sci, 660:136–153, 1992.

*Primary Examiner*—Scott D. Priebe
*Assistant Examiner*—Dave Trong Nguyen
*Attorney, Agent, or Firm*—Oblon, Spivak, McClelland, Maier & Neustadt, P.C.

[57] ABSTRACT

The present invention relates to a process for producing a conjugate of a biologically active peptide or protein having at least one glutamine residue with a high-molecular weight substance containing an amino group. The present invention also relates to a composite of this conjugate with a nucleic acid adsorbed thereto for transferring nucleic acids to mammalian cells.

10 Claims, 4 Drawing Sheets

MODIFIED PROTEIN FOR GENE TRANSFER AND PROCESS FOR PRODUCING THE SAME

This application is a continuation of U.S. Ser No. 08/536, 280, filed Sep. 29, 1995, abandoned, which claimed priority to Japanese application 6-270102, filed Sep. 29, 1996.

BACKGROUND OF THE INVENTION

1. Field of the Invention

The present invention relates to a conjugate of i) a biologically active peptide or protein which can be bound to a specific receptor of a cell in a human body, and ii) a high-molecular weight substance having an affinity for a nucleic acid, especially a DNA, such that the nucleic acid can be adsorbed or dispersed into the same, as well as a process for producing said conjugate.

The composite can bind to a cell having a complementary receptor and can transfer a nucleic acid into a specific type of cells, a specific organ or tumor cells of the human body.

2. Discussion of the Background

It has been considered that biologically active peptides can be used as target molecules for drug delivery. For example, a method has been described in which diphtheria toxin was bound to an IL-6 molecule and specifically sent to tumor cells having an IL-6 receptor to thereby kill the tumor cells. Further, a method was described in which an anti-tumor agent was bound to a monoclonal antibody that recognized a cancer-specific antigen and was specifically sent to tumor cells.

Methods using biologically active peptides in drug delivery systems (DDS) have become important in the field of gene therapy. Wu et al have developed a method for gene therapy in which polylysine (having a positive charge) is chemically bound to a biologically active peptide such as asialoorosomucoid to form a conjugate. A DNA plasmid (having a negative charge) can then be adsorbed into this conjugate to form a composite. Such a conjugate can be used to send the DNA to a hepatocyte having an asialoglycoprotein receptor (J. Biol. Chem., 236, 14621, (1988)). This conjugate can transfer the gene into the liver following intravenous injection and is expected to be an efficient gene delivery system.

The diseases which can be treated with such specific composites depend on the gene which is delivered. For example, a viral thymidine kinase gene targeted into the liver can activate the anti-viral drug, ganciclovir, directly in the liver. Such directed therapy results in less side effects.

When a nucleic acid is administered to the human body for gene therapy two difficulties arise. First, the nucleic acid is rapidly decomposed. Second, the DNA cannot easily enter a cell. Further, when the nucleic acid is inserted into the genome, the cell can be adversely affected by insertion of the DNA at a site which impairs critical gene expression or by expression of a product which impairs the functioning of the cell. Accordingly, the following elements are desirable in a composition suitable for delivering nucleic acids:

i) The nucleic acid should be delivered to the cell such that it is not easily decomposed.

ii) The nucleic acid should be transferred into the cell at a high rate and, as much as possible, to the specific cell targeted for therapy.

As one solution to the above-mentioned problems, the nucleic acid has been adsorbed into a polymer which suppresses the decomposition of the nucleic acid. As another solution, a ligand which binds to a specific receptor on the targeted cell is combined with a polymer with the nucleic acid adsorbed therein. In both of these, the composite comprising the nucleic acid adsorbed into the polymer is transported to the target cell type by means of endocytosis through ligand-receptor binding. In this case, it is necessary to promote binding of the ligand, which is the composite comprising the nucleic acid adsorbed in the polymer, to the biologically receptor.

Unfortunately, when the biologically active peptide is chemically bound to the polymer, its biological activity tends to be impaired and by-products are formed through various side reactions. This reduces the quality of the drug system. It is desirable to develop a practical method for binding a high-molecular weight substance having a nucleic acid adsorbed therein to a biologically active peptide specifically under mild conditions. It is also desirable to find such a process which has few side reactions.

SUMMARY OF THE INVENTION

Accordingly, one object of the present invention is to provide a process for producing a conjugate comprising a high molecular weight substance selectively bound to a biologically active peptide under mild conditions.

A second object of the present invention is to provide a conjugate of a biologically active peptide or protein and a high-molecular weight substance into which nucleic acids can be adsorbed.

A third object of the present invention is to provide a composite comprising a nucleic acid adsorbed into the above conjugate.

The present invention also provides a pharmaceutical composition for gene transfer therapy which comprises said conjugate and a pharmaceutically acceptable carrier.

The present invention also provides a pharmaceutical composition for gene transfer therapy which comprises said composite and a pharmaceutically acceptable carrier.

These and other objects of the present invention have been realized by the present inventors who have discovered that a conjugate comprising a high molecular weight substance selectively bound to a biologically active peptide can be produced under mild conditions using a transglutaminase.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE INVENTION

Figure 1:
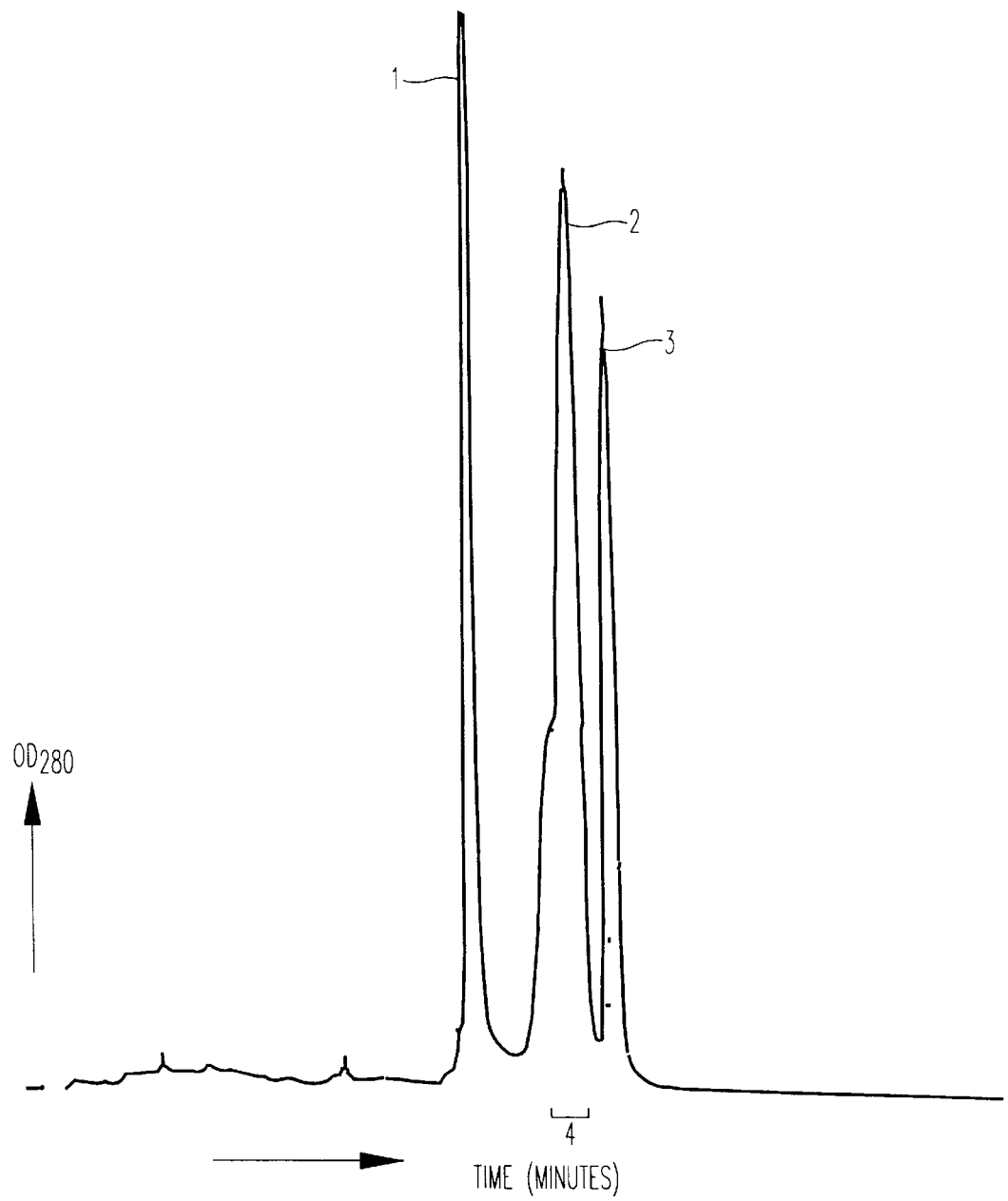
FIG. 1 shows a pattern of chromatography of a reaction solution of polylysine and IL-6.

The present inventors have conducted various investigations to solve the above-mentioned problems, and have consequently found that a conjugate comprising a high molecular weight substance selectively bound to a biologically active peptide under mild conditions can be produced using a transglutaminase.

Suitable transglutaminases which can be used in accordance with the present invention include those classified as EC 2.3.2.13 (family name: protein-glutamine: γ-glutamyl-transferase). Such enzymes catalyze formation of a bond between the γ-amide of a glutaminyl residue of a peptide or protein and an amino group of a second substrate. Transglutaminases in accordance with the present invention have been reported in a variety of documents which are incorporated herein by reference. For example:

(a) Folk et al, Adv. Protein Chem. 31, 1–133 (1977).

(b) Folk et al, Adv. Enzymol, 38, 109–191 (1973).

(c) Bohn et al, Mol. Cell Biochem. 20, 67–75 (1978).

(d) Lorand et al, Handbook of Biochemistry and Molecular Biology, vol. 2, Proteins, ed. G. D. Fasman, pp. 669–685, Cleveland: CRC. 3rd ed.

(e) Guinea pig and rabbit liver transglutaminase: Abe et al, Biochemistry, 16, 5495–5501 (1977).

(f) Human red blood cells transglutaminase: Brenner et al, Biochem. Biophys. Acta. 522, 74–83 (1978).

(g) Rat coagulating gland transglutaminase: Wilson et al, Fed. Proc., 38, 1809 (Abstr.) (1979).

Various types of transglutaminases are known and vary depending on the source from which they are obtained. Examples include a transglutaminase derived from microorganisms (bacterial transglutaminase, hereinafter simply referred to as "BTG", such as those reported in Ando et al, Agric. Biol. Chem., 53(10), 2613–2617 (1989), and Washizu et al, Biosci. Biotech. Biochem., 58(1), 82–87 (1994), incorporated herein by reference), and mammalian transglutaminases such as liver transglutaminase, plasma factor XIIIa, platelet placental factor XIIIa, hair-follicle transglutaminase, epidermal transglutaminase and prostate transglutaminase. Any of these transglutaminases can be used in the present invention. BTG is preferred.

The binding reaction catalyzed by the transglutaminase is specific for the γ-amide of a glutaminyl residue. Accordingly, few by-products are formed and the reaction can be easily controlled. Further, because it is an enzymatic reaction, the following advantages are obtained:

i) A conjugate is formed at a specific position without a reduction in the function of the substance to be bound.

ii) Since the binding is conducted under physiological conditions, the biological substance to be bound is not denatured.

iii) As the high level of selectivity is maintained, a high-quality drug can be produced. The products have a unique, defined structure.

The process of the present invention has the following benefits over proteins which are bound to each other using recombinant DNA methods in which genes are combined with each other. Compared to these recombinant DNA methods, the process of the present invention possesses the following advantages.

i) the process of the present invention can bind biological substances which cannot be directly translated from DNA, such as a sugar chain, glycoprotein, glycolipid, PEG (polyethylene glycol) and the like.

ii) Recombinant DNA methods merely produce a fusion protein in which a protein is bound to the N-terminal or C-terminal of another protein.

iii) Since recombinant DNA methods merely produces such fusion proteins in which a protein is bound to the N-terminal or C-terminal of another protein, the active site is present in the terminal of the protein. Consequently, there is a strong possibility that such fusion proteins have low activity.

On the other hand, when using a transglutaminase in the method of the present invention, the substance having the amino group is bound to the γ-amide group of glutamine only. Thus, a conjugate different from that obtained by the recombinant DNA method is obtained wherein the activities of both of the compounds are maintained.

The high-molecular weight compound in accordance with the present invention must allow a nucleic acid to be adsorbed therein. It also must be able to bind to the biologically active peptide under enzymatic reaction conditions with the transglutaminase.

Standard transglutamination reaction conditions can be used. For example, when BTG is used, the reaction can be carried out at a temperature of from 4 to 55° C., preferably from 30 to 50° C. and at a pH of from 5 to 8, preferably from 6 to 7.

Transglutaminase activity can be monitored by reacting benzyloxycarbonyl-L-glutamineglycine and hydroxylamine with a transglutaminase derived from an animal in a Tris-buffer (pH 6.0) at 37° C. in the presence of 5 mM $Ca^{2+}$. The reaction mixture is reacted with transglutaminase in the absence of 5 mM $Ca^{2+}$. Any thus obtained hydroxamic acid is formed into an iron complex in the presence of trifluoroacetic acid. Then, the absorbance at 525 nm is measured, and the amount of hydroxamic acid reacted is calculated from the calibration curve. The amount of oxygen with which 1 M of hydroxamic acid is formed for 1 minute is defined as 1 unit (1 U) which is the unit of transglutaminase activity.

The high-molecular weight substance which contains an amino group and into which a nucleic acid, especially a DNA, can be adsorbed may be any substance. It is advisable that the substance satisfy the following conditions.

i) The substance should have a strong ability to protect DNA from decomposition.

ii) The substance should not be retained at any site in the circulatory system of the human body.

iii) The substance should not harm the human body.

iv) The substance should not act harmfully when the DNA enters the cell or is expressed within the cell.

Suitable substances are preferably peptides or proteins containing an amino group. Since a DNA plasmid is generally negatively charged, a positively charged high-molecular weight substance can typically be used. Polylysine or a peptide containing at least 30%, preferably 50%, by weight lysine can be used. Suitable compounds have weight average molecular weights from 5,000 to 200,000, preferably from 10,000 to 100,000 g/mol. The preferred high-molecular weight substance is polylysine.

Suitable biologically active peptides and proteins useful in accordance with the present invention are conventionally known. Examples include biologically active peptides obtained in the nature, for example, peptides which exhibit a physiological action in the human body, such as interleukin (IL) -1, -2, -3, -4, -5, -6, -7, -8, -9, -10, -11 and -12, G-CSF, GM-CSF, M-CSF, erythropoietin (EPO), stem cell factor (SCF), mpl-ligand, α-, β- and γ-interferons, somatostatin, vasopressin, insulin, growth hormone and substance P; peptides obtained by chemically modifying the above-mentioned peptides; substances derived from animals, such as bombesin; substances derived from microorganisms such as diphtheria toxin; and substances derived from plants, such as lectin.

Antibodies are also biologically active peptides within the context of the present invention. Antibodies include not only human monoclonal antibodies but also animal monoclonal antibodies. Most of the biologically active peptides must specifically bind to their corresponding receptors to activate their physiological functions. The antibodies are specifically bound to the corresponding antigens.

Any biologically active peptide which contains a glutaminyl residue in its primary amino acid sequence and which specifically binds to tissues, organs, cells or the like can be used in the present invention. The above-mentioned biologically active peptides or proteins are preferable. Interleukin-2 (IL-2) and interleukin-6 (IL-6) are most preferable.

The following biologically active peptides target the indicated cells and organs and can be used in accordance with the present invention:

IL-2 or anti-IL-2 receptor antibody (antibody against α-chain, β-chain or γ-chain) target:

1) IL-2 receptor is expressed in some leukemia cell types such as ATL.
2) When an organ or a myeloid cell is transplanted, rejection occurs. An activated T-cell causes this rejection, and this T-cell expresses an IL-2 receptor.
3) In chronic rheumatism, a lymphocyte that expresses an IL-2 receptor is locally present and precipitates the production of an auto-antibody, which leads to an attack or the progression of the disease.

IL-6 or anti-IL-6 receptor antibody (antibody against gp80 or qp130) target:

1) Leukemia cells having an IL-6 receptor.
2) In chronic rheumatism, a lymphocyte that expresses an IL-6 receptor is locally present and precipitates production of an auto-antibody, which leads to an attack or the progression of the disease.

Anti-megakaryocyte antibody targets:

Cells having megakaryocyte-specific antigen. With respect to a thrombocytopenia, a gene such as IL-6, IL-11, mpl-ligand or the like is transferred into a megakaryocyte to induce selective proliferation and maturation of the megakaryocyte.

Anti-CD34 antibody targets:

Myeloid cell having CD34 receptors. A genetically deficient gene, for example, ADA (adenosine deaminase) is transferred into the myeloid cell to treat the genetic disease. Further, a multiple drug-resistant (MDR) gene is transferred into a bone marrow to make it drug-resistant, after which the cancer is treated by chemotherapy.

Anti-CD4 antibody target:

Cells having CD4 receptors. A gene that suppresses the proliferation of HIV is transferred into a HIV-infected cell to treat AIDS.

Polymeric HSA or anti-albumin receptor antibody targets:

Polymeric HSA is bound to a liver albumin receptor. A hepatoma is treated by transferring an anti-oncogene corresponding to the hepatoma.

Anti-ErbB2 antibody target:

Cancer having ErbB2. The cancer is treated by transferring an anti-oncogene into cancer cells.

EGF targets:

An anti-oncogene is transferred into cancer cells having an EGF-receptor of an ovarian cancer or the like to treat the cancer.

Antibody against an antigen specific for a cancer of the large intestine, colon and rectum targets:

An anti-oncogene is transferred into a cell of a cancer of the large intestine, colon and rectum to treat the cancer.

The negatively charged DNA molecule can be suspended in an aqueous solution and adsorbed into the positively charged high-molecular weight substance conjugated to the biologically active peptide to form a composite. This composite can specifically transfer the gene into a tissue corresponding to the target molecule through in vivo administration.

In the following Examples, polylysine is used as the high-molecular weight substance. However, the high-molecular weight substance is not limited to polylysine. Any substance which is available and has some affinity for DNA, which is not harmful to the human body and which is not easily trapped in the circulatory system can be used.

Examples of the conjugate of the biologically active peptide or protein and the high molecular weight substance are shown below, but the conjugate and the composite in the present invention are not limited thereto.

Polylysine-IL-6/thymidine kinase gene expression plasmid: Treatment of chronic rheumatism by transferring a suicide gene into an IL-6 receptor expression synovial membrane cell. Treatment of a cancer having an IL-6 receptor, for example, myeloma by inserting the suicide gene therein.

Polylysine-anti-CD14 antibody/ADA gene expression plasmid: SCID patient. Treatment by transferring an ADA gene into a hematopoietic stem cell.

Polylysine-anti-CD14 antibody/β-globin gene expression plasmid: Treatment of thalassemia by introducing a normal β-globin gene into a hematopoietic stem cell.

Polylysine-anti-CD4 antibody/thymidine kinase expression plasmid: Treatment of AIDS by transferring a suicide gene into a HIV-infected T-cell.

Polylysine-anti-CD4 antibody/reverse transcriptase antisense gene expression plasmid: Treatment of AIDS by transferring a HIV proliferation suppressive gene into a HIV-infected T-cell.

Using a transglutaminase, a biologically active peptide or protein containing glutamine can be bound to a high-molecular compound containing an amino group under specific, mild conditions. Since a nucleic acid can be adsorbed into this conjugate without losing any of the properties of the biologically active peptide or protein, the nucleic acid can be transported into cells selectively with high efficiency, utilizing the properties of the biologically active peptide or protein which is specifically accumulated in tissues, organs, cells or the like. Accordingly, the present invention can be applied to gene therapy and the like.

The present invention will be illustrated more specifically by referring to the following Examples. However, the present invention is not limited to these Examples.

EXAMPLES

Example 1

Preparation of polylysine-bound IL-6 using polylysines having different molecular weights:

10 mg of polylysine bromide (having a molecular weight of 7,900, 45,700 or 83,800, made by Sigma Co.) were dissolved in 4 ml of 50 mM tris-HCl (pH 7.5). To the solution were added 50 µL of a BTG solution (14 U/ml of 50 mM tris-HCl, pH 7.5). The mixed solution was allowed to stand at room temperature for 30 minutes. To the mixed solution were added 2 ml of an rhIL-6 (recombinant human IL-6) solution (2 mg/ml of 10 mM sodium citrate, pH 7.0). The mixture was stirred, and then allowed to stand at 37° C. for 2.5 hours (in the case of polylysine having a weight average molecular weight of 7,900) or for 20 hours (in the case of polylysine having a weight average molecular weight of 45,700 or 83,800). The reaction solution was purified through reverse-phase HPLC.

The pattern of chromatography of the reaction solution when using polylysine having a weight average molecular weight of 7,900 is shown in FIG. 1. In FIG. 1, peak 1 (22.14 minutes) indicates polylysine, peak 2 (27.57 minutes) indicates polylysine-bound rhIL-6, and peak 3 (29.66 minutes) indicates rhIL-6. In FIG. 1, 4 indicates a polylysine-bound rh-IL6 fraction.

Column: Vydac Protein C4214TP54 (4.6×250 mm)

Solvents: A: 0.1% trifluoroacetic acid (TFA) and B: 0.1% TFA-80% acetonitrile

Flow rate: 1 ml/min

The elution program of the chromatography is shown in Table 1.

TABLE 1

| | Elution program | |
|---|---|---|
| Time (min) | A % | B % |
| 0.0 | 100 | 0 |
| 5.0 | 100 | 0 |
| 5.1 | 60 | 40 |
| 35.0 | 0 | 100 |
| 50.0 | 0 | 100 |

The polylysine-bound IL-6 fraction was collected, and concentrated through the same reverse-phase HPLC. The elution was conducted upon linearly increasing the concentration of B buffer in A buffer from 0% to 100% over 5 minutes (A and B solvents (buffers) were the same as those in FIG. 1). The polylysine-bound IL-6 fraction was further purified through gel filtration chromatography.

Column: Sephadex G-75 (1×10 cm)

Buffer: 20 mM tris-HCl, 0.5M NaCl pH 8.5)

Flow rate: 2 ml/min

The purity of the thus-purified polylysine-bound IL-6 was measured through HPLC. The pattern of this chromatography is shown in FIG. 2.

Figure 2:
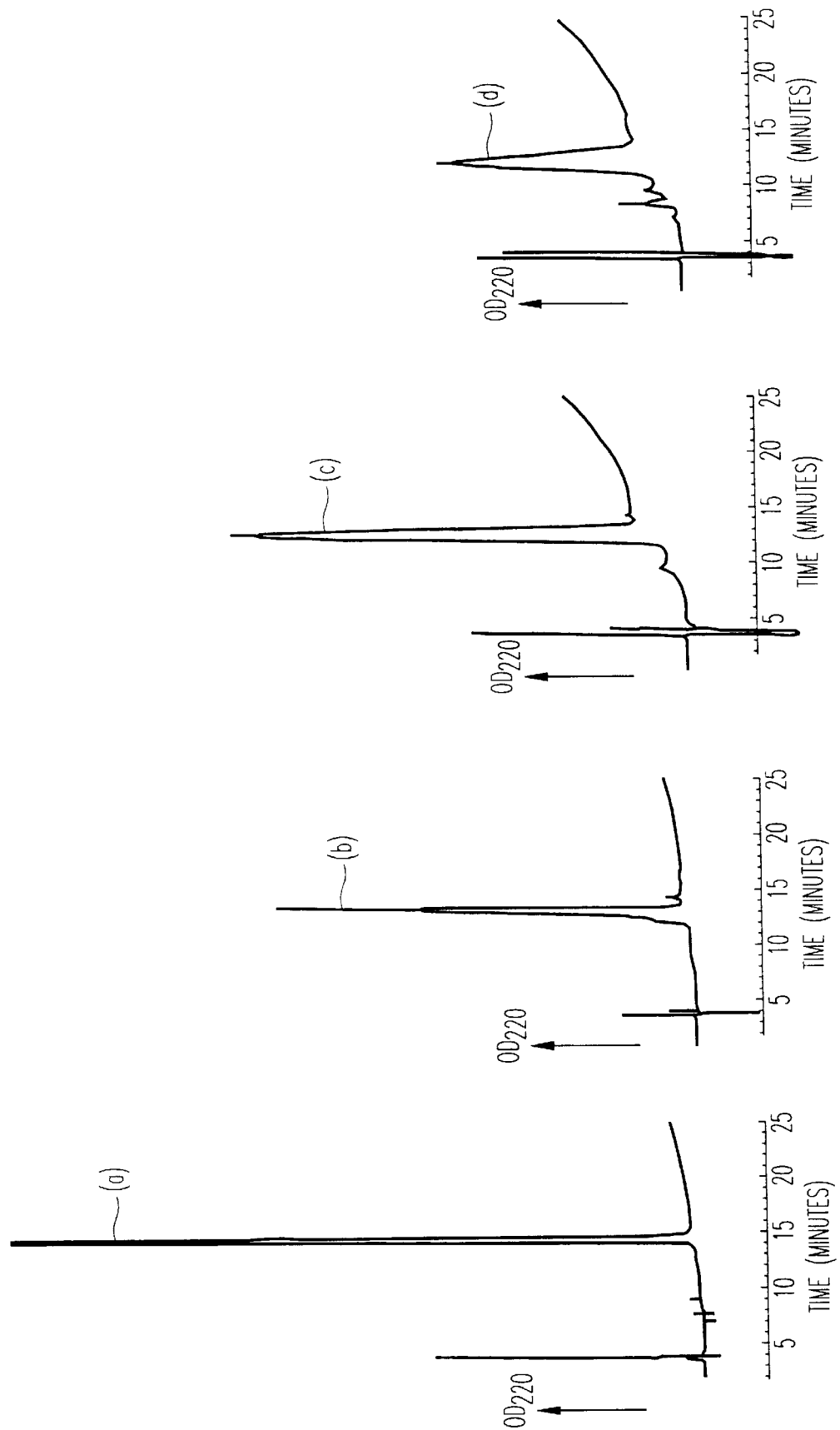
FIG. 2 shows a pattern of chromatography of purified polylysine-bound IL-6.

In FIG. 2-1, peak (a) indicates rhIL-6 (retention time 14.12 minutes).

In FIG. 2-2. peak (b) indicates rhIL-6 bound to polylysine having a weight average molecular weight of 7,900 (retention time 12.38 minutes).

Figure 3:
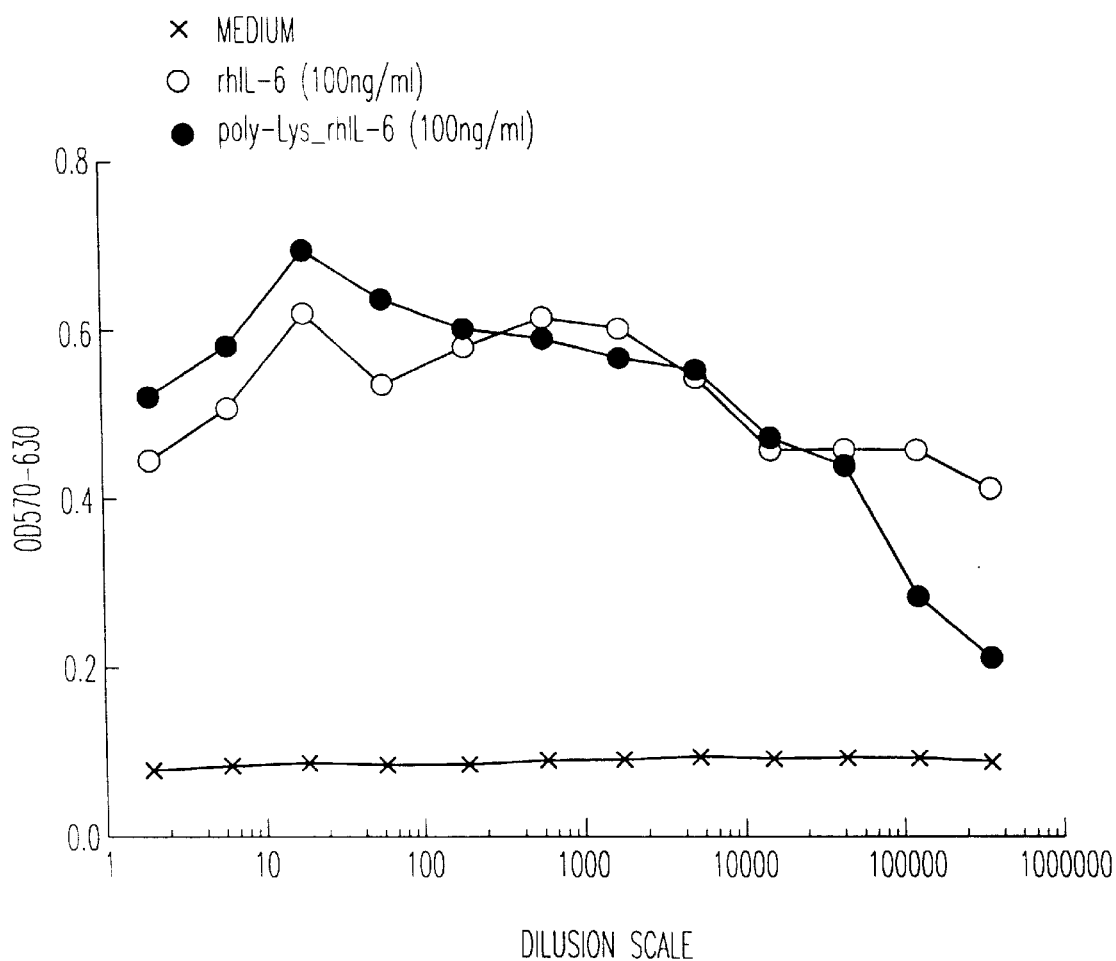
FIG. 3 shows results of in vitro activity of IL-6 and polylysine-bound IL-6.

In FIG. 2-3, peak (c) indicates rhIL-6 bound to polylysine having a weight average molecular weight of 45,700 (retention time 12.16 minutes).

Figure 4:
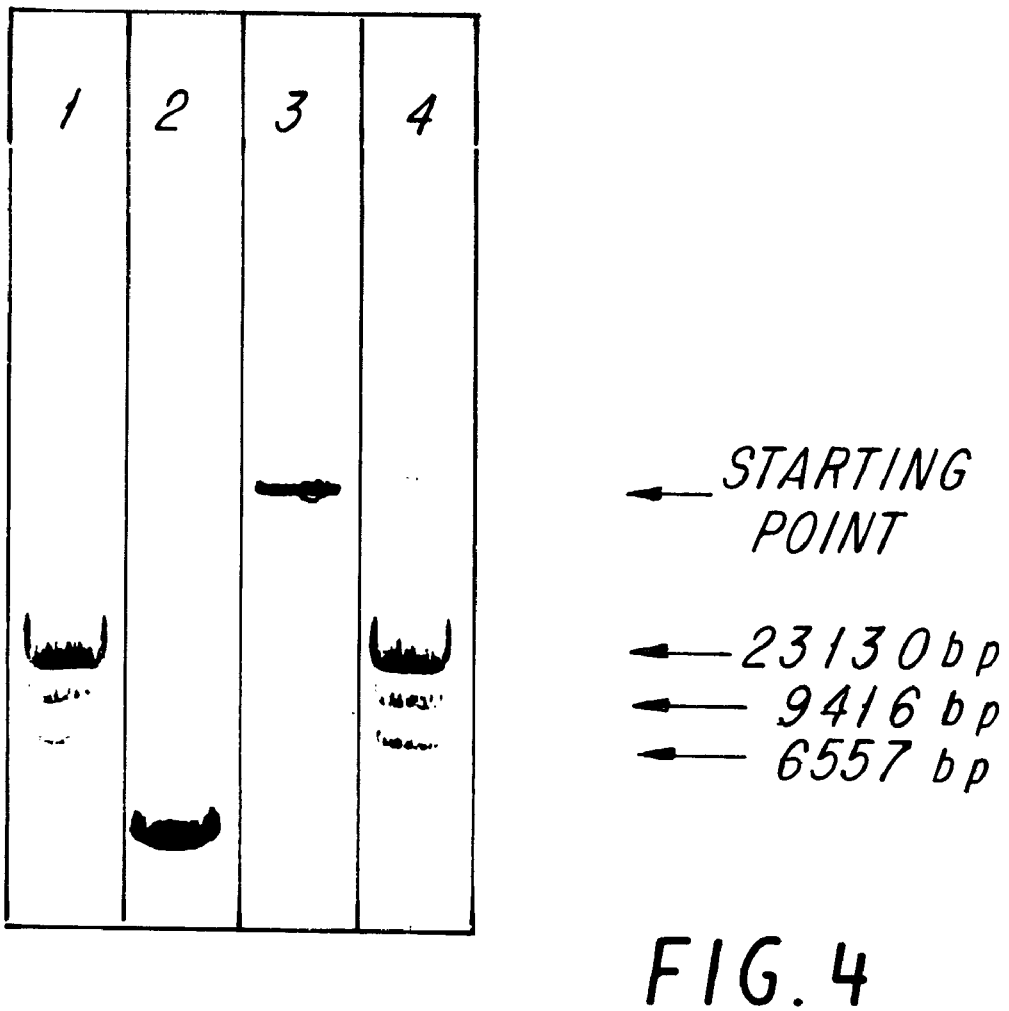
FIG. 4 shows an electrophoresis pattern for the formation of the composite of polylysine-bound IL-6 and DNA.

In FIG. 2-4, peak (d) indicates rhIL-6 bound to polylysine having a weight average molecular weight of 83,800 (retention time 11.46 minutes).

The conditions of HPLC are as follows.

Column: Vydac Protein C4214TP54 (4.6×250 mm)

Solvents: A: 0.1% trifluoroacetic acid (TFA)
B: 0.1% TFA-80% acetonitrile

Flow rate: 1 ml/min

The elution program is shown in Table 2.

TABLE 2

| | Elution program | |
|---|---|---|
| Time (min) | A % | B % |
| 0.0 | 60 | 40 |
| 20.0 | 0 | 100 |

All of the purified polylysine-bound IL-6 showed approximately single peaks.

Results:

BTG proved to have ability to bind all of the polylysines having the different molecular weights to IL-6.

Example 2 i) In vitro activity of polylysine-bound IL-6

Method

MH60.32 strain was used which was obtained by subcloning IL-6-dependent mouse hybridoma MH60 BSF2 (Matsuda et al., Eur. J. Immunol., 18, 951, (1988)). The following solution was added to each well of a 96-well plate.

a) 100 μL of a sample solution which was stepwise diluted in a culture medium.

b) 5×10³ MH60 hybridomas which were washed three times in a culture medium and suspended in 100 μL of the culture medium. After the hybridomas were cultivated in the presence of 5% $CO_2$ at 37° C. for 60 hours, the number of cells were measured using a MTT assay. The MTT assay was conducted as follows.

50 μL of MTT (3-(4,5-dimethylthiazol-2-yl)-2,5-diphenyltetrazolium bromide in an amount of 1 mg/ml PBS solution) solution were added to each well. After the completion of the cultivation, 150 ml of a supernatant were removed. To the residue were added 100 μL of an MTT solution (20% SDS 0.04N HCl solution), and the mixture was cultivated overnight. The absorbance (at from 570 nm to 630 nm) was measured through a microplate reader.

The culture mediums used in Example 2 were PRMI1640 (Gibco) and 10% FCS (inactive).

Results:

With respect to the proliferation activity of MH60, the results of the in vitro activity of polylysine-bound IL-6 (weight average molecular weight 7,900) are shown in FIG. 3. From the results, it follows that the activity of polylysine-bound IL-6 was equal to that of IL-6. Polylysine-bound IL-6 which was bound to polylysine having a weight average molecular weight of 45,700 or 83,800 also exhibited the activity which was equal to that of IL-6.

ii) In vivo activity of polylysine-bound IL-6

Method:

A sample (0.1 ml) was subcutaneously injected into a healthy ICR-strain mouse which was approximately 6 weeks old and had a weight of 25 g. The sample was diluted with PBS and suspended in PBS. One group of test animals consisted of 5 animals. The sample was administered twice a day (day and night) for a total of 9 times until the morning of Day 5. 4 to 8 hours after the last administration, blood was collected from the heart of each test animal and was mixed with an anticoagulant. Within 3 hours from the collection of the blood, the number of platelets was counted using a method of detecting change in resistivity. The average number of platelets per unit volume was counted.

Results:

The results in the case of using polylysine-bound IL-6 which was bound to polylysine having a weight average molecular weight of 7,900 are shown in Table 3. As is clear from Table 3, polylysine-IL-6 increased the number of platelets in vivo compared to IL-6.

Polylysine-bound IL-6 which was bound to polylysine having a weight average molecular weight of 45,700 or 83,800 exhibited the same activity as that shown in Table 3.

TABLE 3

| In vivo activity of polylysine rhIL-6 (increase in number of platelets) | |
|---|---|
| Medicament | Number of platelets ± S.D. (× $10^4$/μL) |
| Citrate buffer (10 mM sodium citrate, pH 7.0) | 111.2 ± 8.9 |

TABLE 3-continued

In vivo activity of polylysine rhIL-6
(increase in number of platelets)

| Medicament | Number of platelets ± S.D. (× $10^4/\mu L$) |
|---|---|
| rhIL-6(5 μg/shot) | 124.6 ± 19.1 |
| Polylysine rhIL-6 (5 μg/shot) | 131.2 ± 7.7 |

Example 3

Formation of a composite of polylysine-bound IL-6 and a DNA:

Method:

100 μL of polylysine-bound IL-6 (0.3 mg/ml of 0.2M sodium phosphate, pH 6.0) were added to 1 μL of a DNA solution (2 μg/μL). The mixture was stirred by means of a vortex stirrer for 15 seconds, and then allowed to stand at room temperature for 30 minutes to form a composite of the two components. The composite of polylysine-bound IL-6 and DNA and DNA alone were electrophoresed on a 0.8% agar gel to confirm the formability of the composite through ultraviolet light in the presence of EtBr.

Results:

i) The pattern of the electrophoresis is shown in FIG. 4. In FIG. 4, lanes 1 and 4 are markers (digested with λ-Hind III), lane 2 is a plasmid vector (pSV-β-galactosidase vector), and lane 3 is a composite of DNA and polylysine-bound IL-6.

As shown in FIG. 4, when the DNA formed the composite with polylysine-bound IL-6, it was not electrophoresed on the 0.8% agar gel and stayed at the original point. This is because polylysine-bound IL-6 prepared using BTG formed the composite with the DNA. Thus, polylysine-bound IL-6 proved to have the ability to form the composite with the DNA.

In FIG. 4, polylysine-bound IL-6 which was bound to polylysine having a weight average molecular weight of 7,900 was used. When using polylysine-bound IL-6 which was bound to polylysine having a weight average molecular weight of 45,700 or 83,800, the same results were also provided.

Example 4

Specific transfer of a gene into an IL-6 receptor-containing cell by means of polylysine-bound IL-6 (1):

Method:

A composite comprising 20 μg of a DNA and 10 μg of polylysine-bound IL-6 which composite was prepared by the same method as in Example 3 was added to cultured cells. Subcultured cells were charged into 2 ml of a culture media on 1×10⁵ 6-well plates, and were cultured for some hours. The above-mentioned polylysine-bound IL-6/DNA composite was added thereto. The mixture was cultured in the presence of 5% $CO_2$ at 37° C. for 48 hours. Then, the expression amount of β-galactosidase was measured as follows.

With respect to the cells, U266 was used as an IL-6 receptor-containing cell, and CEM as a cell free from the IL-6 receptor, respectively. pSV-β-galactosidase vector (6821 bp)(made by Promega, USA) was used as DNA. The β-galactosidase activity was measured according to Technical Bulletin of Promega (reference literature, F. C. Lucibello et al., Met. Mol. Cell Biol., vol. 1, 9, 1989).

Results:

The results are shown in Table 4. As is apparent from Table 4, the IL-6 receptor-containing cell U266 exhibited significantly high B-galactosidase activity compared to the IL-6 receptor-free cell CEM.

Further, in the U266, the β-galactosidase activity of the cell cultured with the composite of polylysine-bound IL-6 and DNA was higher than that of the cell cultured with polylysine-bound IL-6 or DNA alone.

TABLE 4

β-galactosidase (lacZ) gene transfer by means of polylysine IL-6

| Culture medium for growth of cells | Absorbance at 405–595 nm | |
|---|---|---|
| | U266 | CEM |
| Blank | 0.08 | 0.07 |
| Culture medium as such | 0.30 | 0.25 |
| DNA-containing culture medium | 0.29 | 0.23 |
| Culture medium containing polylysine (molecular weight 7,900)-bound rhIL-6 | 0.34 | 0.24 |
| Culture medium containing polylysine (molecular weight 45,700)-bound rhIL-6 | 0.25 | 0.23 |
| Culture medium containing polylysine (molecular weight 83,800)-bound rhIL-6 | 0.35 | 0.25 |
| Culture medium containing polylysine (molecular weight 7,900)-bound rhIL-6/DNA composite | 1.08 | 0.24 |
| Culture medium containing polylysine (molecular weight 45,700)-bound rhIL-6/DNA composite | 1.10 | 0.25 |
| Culture medium containing polylysine (molecular weight 83,800)-bound rhIL-6/DNA composite | 1.03 | 0.23 |

Example 5

Specific transfer of a gene into an IL-6 receptor-containing cell by means of polylysine-bound IL-6 (2):

Method:

Polylysine-bound IL-6 and a composite of a DNA and polylysine-bound IL-6 were prepared in the same manner as in Example 3. Cells were cultured in a DNA-containing culture medium, a culture medium containing polylysine-bound IL-6 and a culture medium containing a composite of the DNA and polylysine-bound IL-6. The amounts added of the DNA, polylysine-bound IL-6 and the composite of the DNA and polylysine-bound IL-6, and the cultivation method were the same as in Example 4. U266 or U937 was used as the IL-6 receptor-containing cell. Hepg2 or Hep3B was used as the IL-6 receptor-free cell.

The weight average molecular weight of polylysine in the polylysine-bound IL-6 used was 7,900. The DNA used was pSV2CAT (Gorman et al., Mol. Cell Biol., 2, 1044, (1982)).

Chloramphenicol acetyltransferase (CAT) activity was measured by the method of Murray (Murray, et al., Nucleic Acids Res., 19, 6648, (1991)).

Results:

The results are shown in Table 5. From Table 5, it becomes apparent that the cells which were cultured by adding the composite of the DNA and polylysine-bound IL-6 exhibited significantly high CAT activity compared to that of the cells which were cultured by adding DNA or polylysine-bound IL-6 alone.

TABLE 5

CAT gene transfer by means of polylysine-bound rhIL-6

| | CPM × $10^{-3}$ | | | |
|---|---|---|---|---|
| Culture medium for growth of cells | U266 | U937 | HepG2 | Hep3B |
| Blank | 0.1 | 0.1 | 0.1 | 0.1 |
| Culture medium as such | 3.0 | 2.2 | 4.5 | 3.5 |
| DNA-containing culture medium | 4.3 | 2.3 | 5.0 | 4.5 |
| Culture medium containing polylysine-bound rhIL-6 | 3.2 | 3.3 | 4.5 | 3.5 |
| Culture medium containing polylysine-bound rhIL-6/DNA composite | 25.2 | 15.2 | 10.0 | 12.0 |

This application is based on JP 6-270102, filed Sep. 29, 1994. The full text of this priority document is incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing a conjugate, which comprises:
   a) reacting (i) IL-2 or IL-6 or both, and (ii) polylysine which contains an amino group or into which a nucleic acid can be adsorbed, and
   b) forming an acid-amide linkage between said amino group and the amide at the gamma-position of a glutaminyl residue of said IL-2 or IL-6 or both in the presence of transglutaminase obtained from bacteria.

2. The process of claim 1, wherein said polylysine has a weight average molecular weight of from 5,000 to 200,000 g/mole.

3. The process of claim 2, wherein the weight average molecular weight is from 10,000 to 10,000 g/mole.

4. A process of producing a conjugate, which comprises:
   a) reacting (i) IL-2 or IL-6 or both, and (ii) polylysine which contains an amino group or onto which a nucleic acid can be adsorbed, in the presence of transglutaminase obtained from bacteria, to form a conjugate; and
   b) adsorbing a nucleic acid to said conjugate.

5. The process of claim 4, wherein said nucleic acid is an expression vector.

6. The process of claim 5, wherein said expression vector comprises a gene encoding thymidine kinase, adenosine deaminase or β-globin.

7. The process of claim 5, wherein said expression vector is eukaryotic or viral.

8. A conjugate, which is produced by:
   a) reacting (i) IL-2 or IL-6 or both, and (ii) polylysine which contains an amino group or into which a nucleic acid can be adsorbed; and
   b) forming an acid-amide linkage between said amino group and the amide at the γ-position of a glutaminyl residue of said IL-2 or IL-6 or both in the presence of a transglutaminase obtained from bacteria.

9. A composition for transferring nucleic acids to mammalian cells, which comprises:
   A) a conjugate, which is produced by:
      a) reacting (i) IL-2 or IL-6 or both,. and (ii) polylysine which contains an amino group or onto which a nucleic acid can be adsorbed; and
      b) forming an acid-amide linkage between said amino group and the amide at the γ-position of a glutaminyl residue in the presence of a transglutaminase obtained from bacteria; and
   B) a carrier.

10. A composition for transferring nucleic acids to mammalian cells, which comprises:
    A) a composite produced:
       a) by reacting (i) IL-2 or IL-6 or both, and (ii) polylysine which contains an amino group or onto which a nucleic acid can be adsorbed, in the presence of a transglutaminase obtained from a bacteria, to form a conjugate, and
       b) adsorbing a nucleic acid in the conjugate; and
    B) a carrier.

* * * * *